United States Patent [19]

Fritzberg

[11] 4,444,690
[45] Apr. 24, 1984

[54] TECHNETIUM CHELATES

[75] Inventor: Alan R. Fritzberg, Denver, Colo.

[73] Assignee: University Patents, Inc., Norwalk, Conn.

[21] Appl. No.: 352,140

[22] Filed: Feb. 25, 1982

[51] Int. Cl.³ .............................................. C07F 13/00
[52] U.S. Cl. ..................................... 260/429 J; 424/1
[58] Field of Search .......................... 260/429.1, 429 J; 424/1

[56] References Cited

U.S. PATENT DOCUMENTS 4,208,398  6/1980  Kubiatowicz ................... 260/429.1

Primary Examiner—Helen M. S. Sneed
Attorney, Agent, or Firm—Mason, Kolehmainen, Rathburn & Wyss

[57] ABSTRACT

A new series of technetium chelating agents based on amide and mercaptide donor groups is described, exemplified by 2,3-bis(mercaptoacetamido)propanoic acid. Chelation of Tc-99 m with 2,3-bis(mercaptoacetamido)-propanoic acid resulted in two components that were separable by high-performance liquid chromatography. The component that eluted first demonstrated high specificity for renal excretion with over 90% in the urine in rabbits at 35 minutes and 87% in the urine of mice at 2 hours and 1.6% or less in the intestines of mice. Excretion was rapid with the first component equal to or greater than I-131 Hippuran in the urine of rabbits at all times. The second or latter component demonstrated comparable specificity, but slower renal excretion kinetics. 2,3-Bis-(mercaptoacetamido)succinic acid forms similar chelates with technetium which are also useful as radiopharmaceuticals for the renal systems of mammals.

8 Claims, 5 Drawing Figures

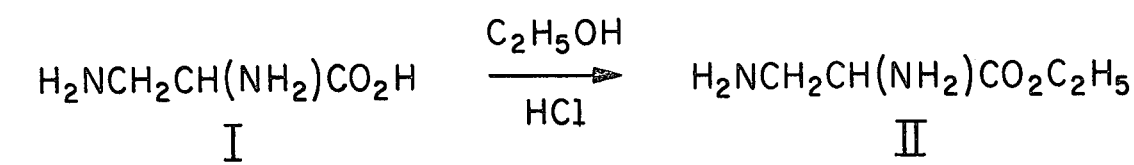
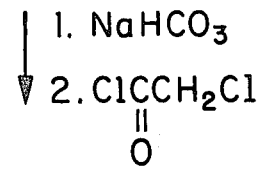
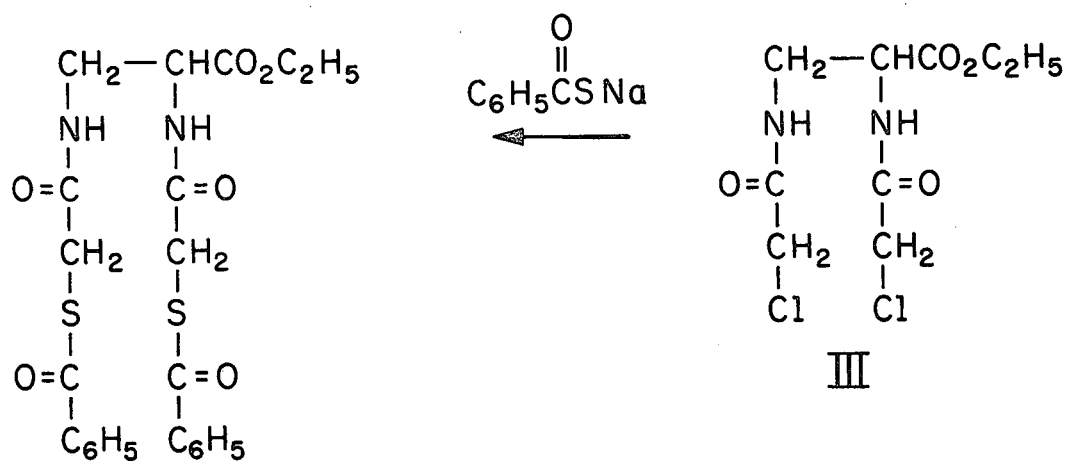
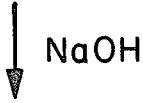
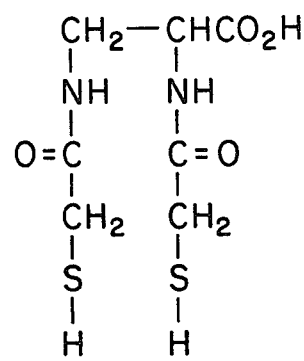
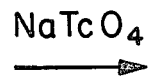
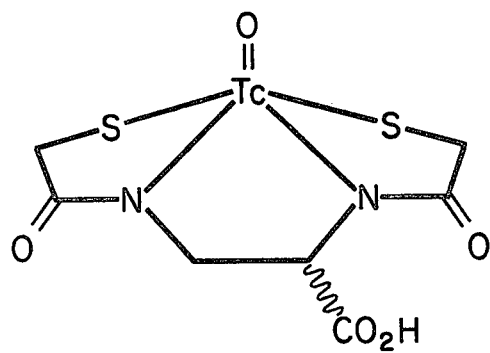
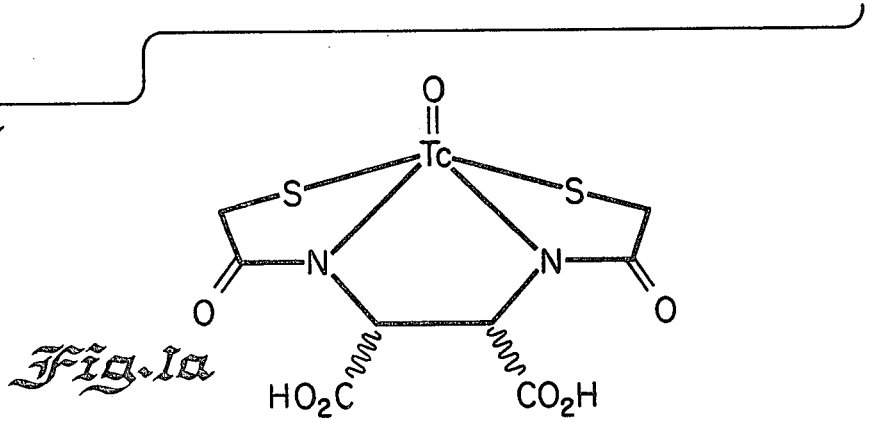
Fig. 1
Fig. 1a

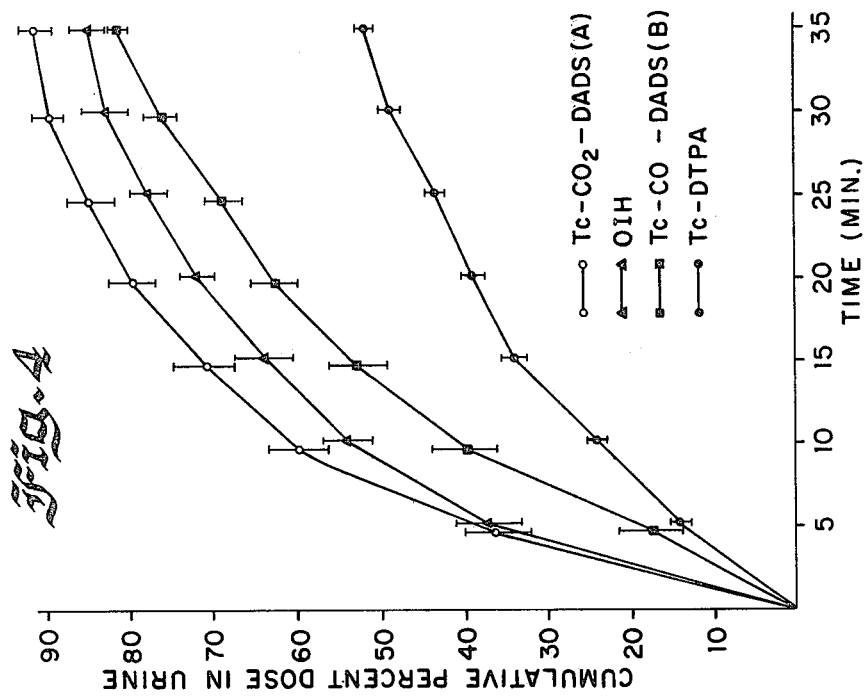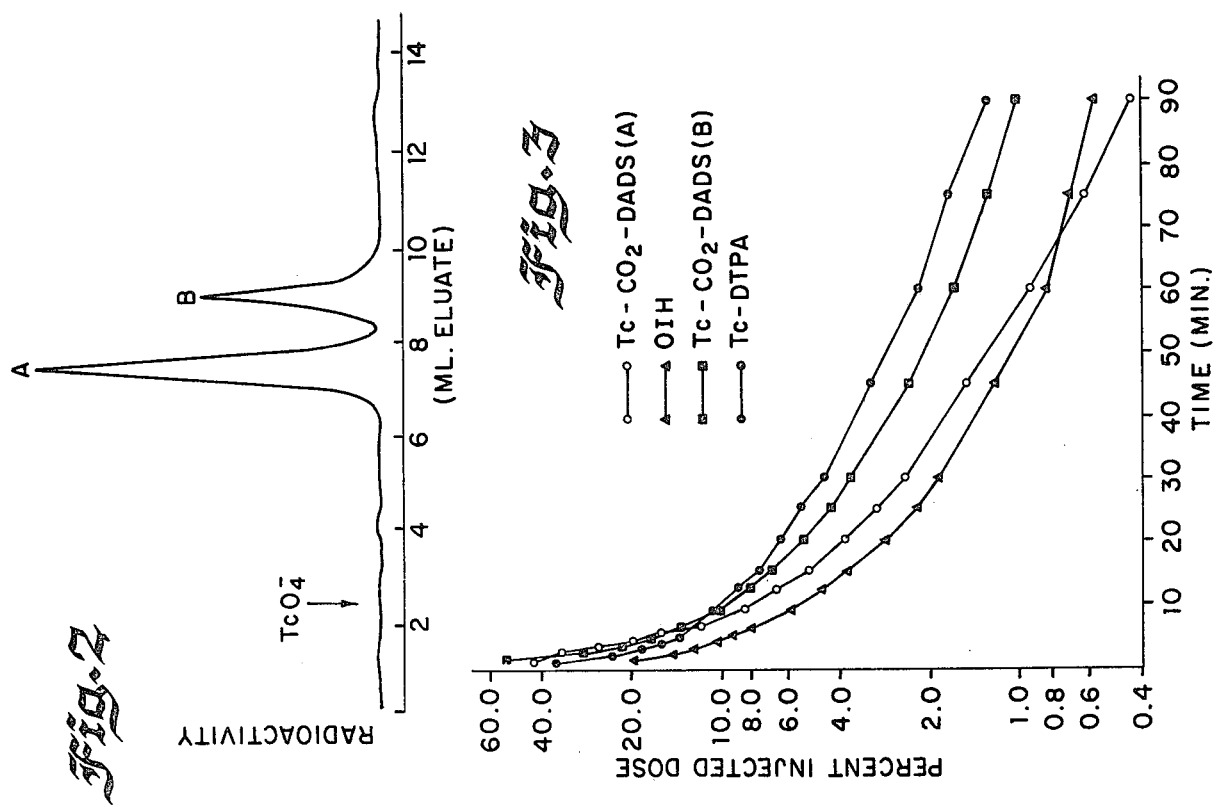

TECHNETIUM CHELATES

This invention relates to novel chelating agents and chelates thereof with technetium. More particularly this invention relates to bis(mercaptoalkanoamido)alkanoic acids of the general formula

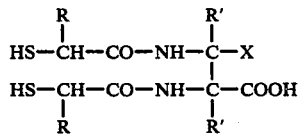

wherein X represents hydrogen or carboxyl and R and R' represent hydrogen or lower alkyl, and water-soluble salts thereof. The invention also relates to chelates of the compounds of the foregoing general formula with radioactive technetium, the method of producing such chelates, and the method of producing compounds of the foregoing general formula.

BACKGROUND OF THE INVENTION 1,2-Bis(mercaptoacetamido)ethane (commonly referred to as DADS) is a tetradentate chelating agent which has been evaluated as a technetium-99m renal function radiopharmaceutical. See A. R. Fritzberg et al, J. Nucl. Med. 22: 258–263, 1981. Biological studies have indicated that this agent is cleared by the kidneys significantly faster than Tc-99m diethylenetriaminepentaacetic acid (Tc-99m DTPA, $p<0.01$) and slightly slower than I-131 o-iodohippurate ($p>0.05$), with no evidence of significant renal retention. While this agent has shown promise as an imaging agent for the renal system there is need for such agents with higher extraction efficiency.

Ideally, renal function should be evaluated with a single radiopharmaceutical which possesses high extraction efficiency, such as I-131 o-iodohippurate (OIH), and also is labeled with a radionuclide having good physical properties such as technetium-99m. Currently two agents are commonly used in the evaluation of renal function, OIH and Tc-99m DTPA. Renal perfusion is evaluated by rapid serial imaging during the first circulation after bolus injection of Tc-99m DTPA. OIH cannot be used for this purpose because the iodine-131 label limits the amount of radioactivity that can be injected. Renal clearance can be evaluated with either Tc-99m DTPA or OIH, but since Tc-99m DTPA is limited to clearance by glomerular filtration, the maximum extraction efficiency is 20%. Secretion of OIH by the renal tubular cells, in addition to some filtration, results in extraction efficiency of about 67%. The higher extraction efficiency of OIH increases the kidney-to-background image ratio, thus increasing the sensitivity of OIH for detection and evaluation of reduced renal function. Davison and coworkers J. Nucl. Med. 20: 641, 1979; Inorg. Chem. 20: 1629–1632, 1981, have described the benzoyl-protected dimercaptodiamides $(PhCOS(CH_2)_nCONH)_2X$ ($n=1$, $X=(CH_2)_2$, $(CH_2)_3$, and $o-C_6H_4$; $n=2$, $X=(CH_2)_2$ and $(CH_2)_3$). From these, via the sodium dithionite reduction of $TcO_4^-$ in base, the technetium complexes $[TcO(S(CH_2)_nCONX-NCO(CH_2)_nS)]^-$ ($n=1$, $X=(CH_2)_2$, $(CH_2)_3$, and $o-C_6H_4$; $n=2$, $X=(CH_2)_2$) were prepared. The synthesis and characterization of the complexes, and their precursors, were reported, and their radiopharmaceutical applicability was discussed.

OBJECTS OF THE INVENTION

It is an object to provide radio-pharmaceutical or radiolabeled contrast agents for evaluation of renal function which do not contain radioactive iodine. It is another object of this invention to provide technetium chelating agents which exhibit high specificity for renal tubular excretion which is equal to or greater than I-131 o-iodohippurate renal excretion. It is a further object to provide technetium chelating agents for renal excretion which are cleared rapidly by the kidneys as I-131 o-iodohippurate. It is another object to provide a method of producing such chelating agents. These and other objects are apparent from and are achieved in accordance with the following disclosure.

GENERAL DESCRIPTION OF THE INVENTION

This invention relates to 2,3-bis(mercaptoalkanoamido)alkanoic acids of the formula

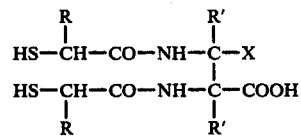

and water-soluble salts thereof, wherein X is hydrogen or carboxyl and R and R' are hydrogen or lower alkyl (e.g., methyl or ethyl). Among the water-soluble salts of the compounds represented by the foregoing formula are the alkali metal and ammonium salts, which are readily formed in aqueous solution.

The 2,3-bis(mercaptoalkanoamido)alkanoic acid compounds of the foregoing general formula can be produced from the corresponding 2,3-diaminoalkanoic acids of the general formula

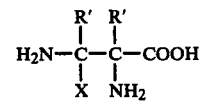

wherein R' and X have the meanings given above, by esterification with a lower alcohol containing dry hydrogen chloride, followed by treatment with a chloroalkanoyl chloride to form the bis(chloroalkanoamido) derivative of the ester, and then by treatment of the latter with sodium thiobenzoate to form the 2,3-bis(benzoylmercaptoalkanoamido)alkanoic acid ester, which on alkaline hydrolysis produces the 2,3-bis(mercaptoalkanoamido)alkanoic acid (as its alkali metal salt).

DESCRIPTION OF THE DRAWINGS

In the attached drawings, FIG. 1 is a diagram illustrating the synthesis of 2,3-bis(mercaptoacetamido)propanoic acid and the formation of the chelate of that acid with technetium-99m.

FIG. 1a illustrates another modification of the invention, namely the Tc-99m chelate of 2,3-bis(mercaptoacetamido)succinic acid.

FIG. 2 is a high-performance liquid chromatogram of Tc-99m-2,3-bis(mercaptoacetamido)propanoate chelate, showing two forms A and B with differing solubility characteristics.

FIG. 3 comprises blood disappearance curves of Tc-99m-2,3-bis(mercaptoacetamido)propanoate [Tc-$CO_2$-DADS] components A and B and reference radiopharmaceuticals OIH and Tc-DTPA in rats. Data are plotted as mean for 5 or more animals at each sampling time. The disappearance slope of component A is comparable to or slightly greater than that of OIH, reflecting similar clearance values. The disappearance of component B is also significantly faster than Tc-DTPA, an indicator of glomerular filtration rate.

FIG. 4 illustrates renal excretion of Tc-99-m-2,3-bis(mercaptoacetamido)propanoate [Tc-$CO_2$-DADS] components A and B and reference radiopharmaceuticals OIH and Tc-DTPA for comparison. Data are mean and range for 3 studies at each point. Component A appears slightly faster than OIH from 10 minutes onward. Component B is always faster than Tc-DTPA, but significantly slower than OIH or component A at early times. By 35 minutes both components and OIH are found in similar amounts.

DETAILED DESCRIPTION OF THE INVENTION

Referring to FIG. 1 of the drawings, the synthesis of 2,3-bis(mercaptoacetamido)propanoic acid is outlined. The starting material, 2,3-diaminopropanoic acid (I), in the form of its hydrochloride, is reacted with absolute ethanol and dry HCl gas. The mixture is refluxed, then evaporated to a dry solid (ethyl 2,3-diaminopropanoate (II) as the hydrochloride) which is then dissolved in a mixture of toluene and saturated sodium bicarbonate solution and reacted with chloroacetyl chloride in toluene to form ethyl 2,3-bis(chloroacetamido)propanoate(III). From this reaction mixture the organic layer is separated and evaporated, isolating compound III. This product is treated with a solution of sodium thiobenzoate in dry ethanol and ethyl 2,3-bis(benzoylmercaptoacetamido)propanoate(IV) is produced. The latter, dissolved in warm ethanol, is treated with aqueous alkali and heated, hydrolyzing the ethyl ester and the benzoyl groups to form V. Then V, treated with pertechnetate solution in the presence of a reducing agent, forms the chelate VI of technetium with 2,3-bis(mercaptoacetamido)propanoic acid, which is a renal imaging agent when the technetium is the gamma radiation-emitting isotope, Tc-99m.

The same series of reactions can be carried out to produce the chelate shown in FIG. 1a. This series starts with 2,3-diaminosuccinic acid (in lieu of 2,3-diaminopropanoic acid) and all the steps are the same, carried out with the same reagents under the same conditions. The resulting chelate with Tc-99m, illustrated in FIG. 1a, is also a useful renal imaging agent.

The invention is described in further detail in the following examples which illustrate specific modes of the invention and their physiological properties.

EXAMPLE 1

Synthesis of ethyl 2,3-bis(benzoylmercaptoacetamido)-propanoate

Into a dry flask under nitrogen were placed 1.40 g (0.010 mol) of 2,3-diaminopropionic acid hydrochloride and 250 ml of absolute ethanol. Then dry HCl gas was bubbled into the solution. The mixture was refluxed for one to two days or until proton magnetic reasonance (pmr) spectra analysis of aliquots with solvent removed indicated complete formation of the ethyl ester. The product was then concentrated to a dry solid. The hydrochloride ester thus obtained was dissolved by rapid stirring at ice bath temperature in a mixture of 50 ml of toluene and 50 ml of saturated sodium bicarbonate. Then 5.0 (0.444 mol) of chloracetyl chloride in 10 ml of toluene was added dropwise. After addition was complete the mixture was allowed to come to room temperature and stirred for an additional 30 minutes. Layers were separated and the aqueous portion extracted twice with ethyl acetate. The organic layers were combined, washed with water and with brine, and dried ($MgSO_4$). Removal of solvent left 2.28 g of ethyl 2,3-bis(chloroacetamido)propanoate as a white solid (87% yield). Pmr ($CDCl_3$): $\delta$1.31 (t, 3.0IH,$CH_3$), 3.74 (t, 1.9H,—HNC$H_2$—CH), 4.07 (s,4.0, Cl$CH_2$NH—), 4.21 (q, 2.0 H, OC$H_2$CH$_3$), 4.67 (broad$_Q$, $1.\overline{0}$ H, —$CH_2$—CH—(—NH—)—$CO_2CH_2CH_3$), and 7.12 and 7.58 (broad, 1.0 H each, —CONH—). The material was used without further purification.

A solution of 953 mg (4.45 mmol) of the ethyl 2,3-bis(chloroacetamido)propanoate was prepared in 10 ml of dry ethanol under nitrogen. To this was added a solution of sodium thiobenzoate in dry ethanol (prepared from 204 mg of sodium (8.87 mmol) in ethanol) to form sodium ethoxide which was reacted with 1.23 g (8.90 mmol) of thiobenzoic acid). After a few minutes at room temperature precipitation occurred. The reaction was heated to reflux for 30 minutes. It was then allowed to cool, diluted with ethyl acetate, washed with water, brine, and dried ($MgSO_4$). Removal of solvent left 2.68 g of a cream colored solid. Recrystallization in toluene gave 1.30 g of ethyl 2,3-bis(benzoylmercaptoacetamido)propanoate: mp 129.5°–131° C.; pmr ($CDCl_3$,—DMSOd$_6$), $\delta$1.20 (t, 3.0 H,OC$H_2$C$H_3$), 3.72 and 3.81 (singlets superimposed on triplet, —COCH$_2$S—) and 3.70 (triplet with singlets, —NHC$H_2$CH(—NH—)—CO—, 6.0 H combined), 4.10 (q, $2.\overline{0}$ H, —OC$H_2$CH$_3$), 4.60 (broad quartet, 1.0 H, —$CH_2$—CH—(—NH—)—$CO_2$), and 6.75–8.15 (complex aromatic and amide H, 12.3 H), Anal: calcd. for $C_{23}H_{24}N_2O_6S_2$: C 56.56, H 4.92, N 5.74, S 13.11; found: C 56.64, H 5.09, N 5.76, S 13.26.

EXAMPLE 2

Synthesis of dimethyl 2,3-bis(benzoylmercaptoacetamido)succinate 2,3-Diaminosuccinic acid dihydrochloride (400 mg, 2.7 mmol) was converted to the methyl ester by refluxing in dry methanol saturated with dry HCl gas. Removal of solvent left 420 mg of solid ester.

A mixture of 40 ml of toluene and 15 ml of an aqueous suspension of 2 g of sodium bicarbonate was added to the ester while cooling. During rapid stirring 0.83 ml (1.18 g, 0.4 mmol) of chloroacetyl chloride diluted in 5 ml of toluene was added dropwise. The mixture was stirred with cooling for 45 min. Separation of layers and extraction of the aqueous residue with ethyl acetate gave 350 mg of dichloroacetamidosuccinic acid which was reacted with sodium thiobenzoate, prepared from 346 mg (2.5 mmol) of thiobenzoic acid and 57 mg of sodium metal (2.5 mmol) in methanol. After refluxing under nitrogen for 2 hours the reaction mixture was reduced to dryness and the residue washed with hexane. Extraction of the product with hot methyl ethyl ketone gave 420 mg. Recrystallization from ethanol and methyl ethyl ketone provided white crystalline dimethyl 2,3-bis(benzoylmercaptoacetamido)succinate of mp 165°–167.5° C.; nmr ($CDCl_3$): 3.77–3.80 (superimposed singlets, 10H), 5.12 (broad t, 2H), 7.2–8.1 (complex, 12H).

EXAMPLE 3
Radiolabeling with Tc-99m

Approximately 100 mCi of Tc-99m pertechnetate in generator eluate saline was made basic by the addition of 5 N NaOH (4 parts saline solution to 1 part NaOH). The radioactivity was extracted twice with methyl ethyl ketone and the extracts combined and reduced to dryness in a nitrogen stream with warming. Then a solution of the hydrolyzed chelating agent 0.5 mg ethyl 2,3-bis(benzoylmercaptoacetamido)propanoate dissolved in 0.3 ml of ethanol, treated with 30 ul of 5 N NaOH and 0.30 ml H$_2$O, and heated 15 minutes at 95° C. in about 0.25 ml volume was added to the Tc-99m pertechnetate residue. Reducing agent (1.0 mg sodium dithionite in 30 ul) was added and the mixture heated at 95° C. for 15 min. The mixture was neutralized with 20 ul of 6 N HCl and injected onto an octadecylsilyl HPLC column (250×4.6 mm, Altex Ultrasphere, 5u) and eluted with 0.01 M sodium phosphate, pH 6 (96%) and ethanol (4%). The column effluent was collected as the A component came out and then sterilized by passage through a 0.22 micron filter. The Tc-99m-2,3-bis(-mercaptoacetamido)propanoate preparations were analyzed for reduced hydrolyzed technetium on silica gel thin-layer strips. Both main components had Rf values of 1 in 0.9% NaCl.

Studies of protein binding were carried out in plasma using an ultrafiltration method described at J.Nucl.Med. 22, 258–263, 1981.

ANIMAL STUDIES—GENERAL

Organ biodistribution and acute toxicity studies were carried out in mice, blood disappearance and bile appearance rates were determined by sampling of bood or bile in rats, and renal excretion rates of the two Tc-2,3-bis(mercaptoacetamido)propanoic acid components, Tc-DTPA, and OIH were determined in rabbits because of greater ease of urine sampling. The HPLC-purified Tc-2,3-bis(mercaptoacetamido)propanoate components were used directly except for dilution as necessary. In general HPLC collected volumes were 1 to 1.5 ml and were not diluted for rabbit studies, were diluted 2- to 10-fold for rat studies and were diluted about 20-fold for mouse studies. In most cases determinations were made with simultaneous administration of OIH.

Biodistribution

The time course of organ distribution was determined in groups of six Hal Cr female albino mice. They were injected with 0.10 ml (0.5 uCi) of the preparation. For comparison purposes, 0.2 uCi OIH was added to each injection. The mice were placed in metabolic cages for the collection of excreted urine. At indicated intervals after injection, the urethra was ligated and the mice killed with chloroform vapor. The organs were removed and counted in a dual channel counter with correction for I-131 crossover into the Tc-99m channel.

Blood Disappearance Rates and Biliary Excretion

These determinations were made in male Sprague-Dawley rats. For blood studies the animals were anesthetized with sodium pentobarbital, a line was placed in a femoral vein for tracer injections and hydration, and another was placed in a carotid artery for blood sampling. About 20μCi (0.25 ml) each of OIH and Tc-99m complex under study were injected and 0.1 to 0.2 ml samples of blood were taken at 1, 2, 3, 4, 5, 6, 9, 12, 15, 20, 25, 30, 45, 60, 75, and 90 minutes after injection. Biliary excretion in the absence of renal function was determined by cannulating the common bile duct, ligating the renal pedicles, and collecting bile in 4-minute fractions for 90 minutes.

Renal Excretion

The rate of renal excretion was measured in New Zealand albino male rabbits. They were anesthetized with ketamine and xylazine and placed on a gamma camera provided with digital storage. After injection of 0.5 to 1 mCi of the Tc-99m complex containing 0.5μCi of OIH, images were collected on tape for 45 minutes. At 35 minutes after injection, urine was expelled from the bladder and the percentage of injected dose contained in the expelled urine was determined. Accumulation of bladder radioactivity was monitored by placing a region of interest over the bladder. The drop in the radioactivity in the bladder after expelling the urine sample (50–80% of the bladder radioactivity) allowed calibration of the bladder time-activity curve in terms of percent injected dose. OIH excretion was based on the change in bladder Tc-99m radioactivity and the amount of I-131 in the urine sample. These values were compared with studies made with OIH alone, in which 250μCi were injected and the bladder radioactivity monitored for I-131.

Tubular Transport Inhibition Studies

The effect of probenicid as an inhibitor of renal tubular transport on the excretion and organ distribution of Tc-2,3-bis(mercaptoacetamido)propanoate-A was studied in mice as described. A dose of 50 mg/kg of probenicid was given 10 minutes prior to injection of radiochemicals. OIH was injected simultaneously. The values at 10 minutes were determined because they have been found to be kinetically representative.

Toxicity

Acute toxicity studies were performed in 52 Hal Cr female mice. The formulation was carried out with added ethanol, NaOH, and HCl and with the heating steps described. The doses administered ranged from 200 to 500 mg/kg. No deaths were observed in the 48-hour period following injection.

In vitro studies

Analysis of a typical Tc-2,3-bis(mercaptoacetamido)-propanoate preparation by high-performance liquid chromatography is shown in FIG. 2. Two major components have been present in variable ratios in every preparation. The first peak, Tc-2,3-bis(mercaptoacetamido)propanoate A, represents the component with superior biological properties. Heating at 95° C. for 30 minutes without added reducing agent resulted in less than 10% of both components in a ratio similar to that shown. The use of stannous ion at room temperature as reducing agent gave the two components shown in about 65% yield with a small early component (5%) and a larger one (30%) with a longer retention time. However, the ratio of the main components was about 2:3 (A:B). The use of dithionite at room temperature as reducing agent resulted in over 90% A and B but in the 2:3 ratio. Formamidine sulfinate as reducing agent at levels of 20 μg and heating for 15 minutes at 95° C. gave over 95% A and B, but in about a 7:3 (A:B) ratio. This result was shown to be independent of reducing agent since the same result was observed with dithionite when the preparation was heated after reducing agent addition, but before neutralization.

For animal studies the radioactivity corresponding to HPLC peaks A and B was collected. The chemical stability of the isolated material is high since no change was observed with time, dilution, or treatment with NaOH and heating at 95° C. for 30 minutes.

At 10 minutes duplicate determinations of binding to plasma proteins resulted in 93% (range 93 to 94) of Tc-2,3-bis(mercaptoacetamido)propanoate-A bound and at 30 minutes 94% (94 to 94) bound. Simultaneously determined OIH was 64% (61 to 67) bound at 10 minutes and at 30 minutes 56% (55 to 57) in agreement with previously reported values. The fraction bound of Tc-2,3-bis(mercaptoacetamido)propanoate-B was 87% (82 to 91) at 10 minutes and 90% (89 and 92) at 30 minutes. These values are similar to the high protein binding value found for Tc-DADS of 95%.

In vivo studies

The results in different species showed good qualitative and, in the case of renal excretion, quantitative agreement. No reaction was noted to the small doses of acetonitrile resulting from HPLC elution of the radiochemicals at about 15% acetonitrile, and the OIH values from simultaneous administration were in good agreement with earlier values (J.Nucl.Med. 22: 258–263, 1981).

Organ Biodistribution

Table 1 shows the organ distribution in mice of Tc-2,3-bis(mercaptoacetamido)propanoate-A from 5 minutes to 2 hours post injection and Tc-2,3-bis(mercaptoacetamido)propanoate-B at 10 minutes and 2 hours for comparison. Over the first 15 minutes component A was slightly higher than or comparable to OIH in renal excretion. Blood disappearance was rapid with 0.6% remaining in the blood at 30 minutes. The initial liver radioactivity of about 8% at 5 minutes appeared to return to the blood since 1.6% or less was seen in the intestine at any time interval and less than 1% was in the liver at 2 hours. The kidneys with 5.6% of the dose at 5 minutes contained less than the 12.6% found for Tc-DADS at 5 minutes. Since 45% of Tc-2,3-bis(mercaptoacetmido)propanoate-A was already in the urine compared to 28% of Tc-DADS at 5 minutes, it appears that the peak kidney radioactivity level is at a time less than 5 minutes after injection. Retention in the kidneys was low with less than 1% of the dose remaining in them at 30 minutes. That Tc-2,3-bis(mercaptoacetamido)-proponoate-B was more slowly cleared is shown by lower levels in the urine at 10 minutes. The higher liver radioactivity seems to account for this. At 2 hours the liver had cleared and renal excretion was only slightly lower than OIH determined simultaneously. Negligible biliary excretion is seen with Tc-2,3-bis-(mercaptoacetamido)propanoate-B as well.

Blood Disappearance

Comparative blood disappearance curves in rats for both components A and B, OIH, and Tc-DTPA, are shown in FIG. 3. OIH showed the most rapid disappearance through 75 minutes. However, Tc-2,3-bis(-mercaptoacetamido)propanoate-A with a higher initial value resulted in comparable curve slopes. The high initial values in the 1- to 5-minute period following injection may be due to a smaller initial volume of distribution due to the high degree of protein binding. For comparison purposes the radioactivity remaining in the blood of Tc-2,3-bis(mercaptoacetamido)propanoate-A was 5% at 16.5 minutes and 2% at 36 minutes while comparative values for Tc-DADS were 5% at 19 minutes and 2% at 68 minutes. The disappearance of Tc-2,3-bis(mercaptoacetamido)propanoate-B (0.05), while faster than Tc-DTPA, was significantly slower than Tc-2,3-bis(mercaptoacetamido)propanoate-A.

Renal Extraction

Comparative rates of renal appearance are shown in FIG. 4. From 10 minutes to 35 minutes Tc-2,3-bis(mercaptoacetamido)propanoate-A was found in the urine to a slightly greater extent than OIH although differences were only significant at 35 minutes ($p<0.05$). In contrast, Tc-2,3-bis(mercaptoacetamido)propanoate-B was significantly lower at early times, but similar to component A and OIH at 35 minutes. These results are consistent with a similar degree of overall specificity, but different renal handling kinetics among these compounds. All were found in the urine in amounts exceeding Tc-DTPA over the 35-minute period measured.

Tubular Transport Inhibition

Clinical studies with Tc-DADS indicated that decreased renal function reduced renal excretion of Tc-DADS to a greater extent than OIH. Experiments with probenicid as an inhibitor of tubular secretion demonstrated a decrease in renal excretion of Tc-DADS to a much greater extent than OIH. Since these results appear to be consistent and suggest that the effect of probenicid may be an indicator of renal excretion efficiency in patients with reduced renal function Tc-2,3-bis(mercaptoacetamido)propanoate was studied under these conditions. The results indicate that the decrease in renal excretion for Tc-99m-2,3-bis(mercaptoacetamido)propanoate-A is much less than for Tc-DADS, but still greater than for OIH (Table 2). Biliary excretion was not increased significantly for component A, but liver radioactivity was.

Biliary Excretion

Biliary excretion of radioactivity in the absence of renal function was slow and amounted to 3.1% (range 2.4 and 3.6) in 90 minutes which compares to 19% for Tc-DADS in the same amount of time. At 90 minute measurement of Tc-99m-2,3-bis(mercaptoacetamido)-propanoate-A radioactivity in other organs was 1% in the kidneys, 21% in the blood, 4% in the liver, 0.1% in the spleen, 0.3% in the stomach, and 22% in muscle.

Acute Toxicity

Acute toxicity studies resulted in no deaths over 48 hours in doses up to 500 mg/kg. Little or no reaction was observed on injection as well.

BIOLOGICAL EVALUATION

Clinical evaluation of Tc-DADS in a limited number of renal transplant patients demonstrated high kidney to background ratios (similar to OIH) and thus high extraction efficiencies in patients with good renal function, but poor ratios (much lower than OIH) in patients with moderate to severe decreases in renal function. Moreover, in patients with decreased levels of renal function hepatobiliary excretion became significant. An unanticipated finding was that the high degree of protein binding of Tc-DADS confined radioactivity to the vascular system rather than the extracellular space as with Tc-DTPA and increased the ease of placing well defined regions of interest on major vessels. This feature facilitated quantitative analysis of renal function.

The biological results of the studies with Tc-2,3-bis(-mercaptoacetamido)propanoate-A indicate that the early or "A" component has significantly improved parameters for renal function evaluation compared to Tc-DADS. In animals with normal renal function the rate of renal excretion is equivalent to OIH and the specificity for renal excretion is nearly complete. The only indication of biological inferiority to OIH is lower renal excretion than OIH in mice pretreated with probenicid as a renal tubular transport inhibitor. However, the depression of renal excretion by probenicid treatment was from 68 to 39% at 10 minutes, a decrease of 43%, while Tc-DADS shows a depression of 61 to 11%, a decrease of 82%, under the same conditions. The depression of OIH was from 65 to 52% or a 20% decrease. Biliary excretion in the absence of renal function amounted to less than 3% in 90 minutes in contrast to 19% for Tc-DADS. In addition, these improvements have been demonstrated without the loss of a high degree of protein binding.

The availability of Tc-2,3-bis(mercaptoacetamido)-propanoate lies in the HPLC purification step. It appears that the two major components in the Tc-2,3-bis(-mercaptoacetamido)propanoate preparations are a result in chelate ring isomers as indicated by VI in FIG. 1. In support of this conclusion are the observations that heating for one minute or less after reducing agent addition results in only Tc-2,3-bis(mercaptoacetamido)-propanoate-B, reduction with dithionite and no heating favors Tc-2,3-bis(mercaptoacetamido)propanoate-B while heating favors Tc-2,3-bis(mercaptoacetamido)-propanoate-A, and the analog prepared from 3,4-diaminobenzoic acid in which the carboxylate group must lie in the plane of the chelate ring carbon atoms gives only one component.

TABLE 1

MICE BIODISTRIBUTION DATA OF TC—CO$_2$—DADS—A and Tc—CO$_2$—DADS—B WITH COMPARISON OIH URINE PERCENTAGES*

| Time | Blood | Liver | Kidneys | Stomach | Intestines | Urine | OIH Urine |
|---|---|---|---|---|---|---|---|
| Tc—CO$_2$—DADS—A | | | | | | | |
| 5 min | 8.19 | 7.81 | 5.61 | 0.24 | 1.61 | 45.52 | 42.02 |
| | ±0.51 | ±0.43 | ±0.67 | ±0.02 | ±0.18 | ±2.16 | ±6.45 |
| 10 min | 3.10 | 4.26 | 2.23 | 0.11 | 0.82 | 67.97 | 64.94 |
| | ±0.19 | ±0.32 | ±0.31 | ±0.004 | ±0.05 | ±0.97 | ±0.89 |
| 15 min | 1.95 | 3.79 | 1.30 | 0.09 | 0.86 | 75.08 | 78.24 |
| | ±0.21 | ±0.46 | ±0.10 | ±0.02 | ±0.16 | ±2.06 | ±0.46 |
| 30 min | 0.59 | 1.34 | 0.51 | 0.07 | 1.05 | 80.82 | |
| | ±0.05 | ±0.13 | ±0.05 | ±0.01 | ±0.12 | ±1.31 | |
| 120 min | 0.21 | 0.78 | 0.25 | 0.04 | 1.46 | 86.57 | 82.43 |
| | ±0.04 | ±0.20 | ±0.05 | ±0.01 | ±0.19 | ±0.92 | ±0.95 |
| Tc—CO$_2$DADS—B | | | | | | | |
| 10 min | 3.64 | 14.83 | 2.87 | 0.13 | 1.00 | 51.94 | |
| | ±0.32 | ±1.33 | ±0.33 | ±0.02 | ±0.10 | ±2.31 | |
| 120 min | 0.14 | 3.71 | 0.14 | 0.02 | 0.21 | 79.16 | |
| | ±0.01 | ±0.43 | ±0.03 | ±0.002 | ±0.01 | ±1.09 | |

*Values are mean and S.E.M. percent injected dose for 6 mice at each time post injection.

TABLE 2

EFFECT OF PROBENICID ON BIODISTRIBUTION PARAMETERS OF RENAL AGENTS*

| | Tc—DADS | | Tc—CO$_2$—DADS—A | | OIH | |
|---|---|---|---|---|---|---|
| Organ | Control | Treated | Control | Treated | Control | Treated |
| Blood | 1.85 | 19.53 | 3.37 | 10.20 | 4.58 | 7.49 |
| | ±0.37 | ±0.69 | ±0.16 | ±0.81 | ±0.24 | ±0.41 |
| Kidneys | 4.25 | 2.69 | 2.53 | 3.93 | 2.83 | 3.79 |
| | ±1.16 | ±0.05 | ±0.24 | ±0.19 | ±0.38 | ±0.18 |
| Liver | 2.24 | 17.13 | 4.21 | 14.36 | 1.31 | 2.68 |
| | ±0.26 | ±1.69 | ±0.24 | ±0.59 | ±0.10 | ±0.19 |
| Intestines | 4.69 | 12.78 | 0.77 | 1.83 | 1.12 | 2.18 |
| | ±0.35 | ±0.91 | ±0.03 | ±0.09 | ±0.11 | ±0.13 |
| Urine | 60.90 | 10.69 | 67.14 | 38.68 | 64.94 | 52.62 |
| | ±2.34 | ±1.18 | ±0.73 | ±2.47 | ±0.89 | ±2.53 |

*Values are mean and S.E.M. percent injected dose at 10 min. post injection for 6 or more mice with each agent. Probencid at a dose of 50 mg/kg was given 10 min. prior to injection of radiopharmaceuticals.

TABLE 3

ORGAN DISTRIBUTION OF Tc—99m—2,3—(MERCAPTOACETAMIDO) SUCCINATE*

| Time (min) | Blood | Kidneys | Liver | Stomach | Intestines | Urine |
|---|---|---|---|---|---|---|
| Component A | | | | | | |
| 10 | 10.13 | 3.41 | 5.80 | 0.40 | 2.16 | 32.32 |
| | ±0.92 | ±0.50 | ±0.93 | ±0.04 | ±0.23 | ±5.33 |
| 120 | 0.44 | 7.44 | 3.17 | 0.03 | 0.30 | 77.73 |
| | ±0.13 | ±1.26 | ±1.00 | ±0.01 | ±0.13 | ±3.99 |
| Component B | | | | | | |
| 10 | 16.21 | 3.43 | 7.06 | 0.53 | 2.88 | 19.32 |
| | ±0.90 | ±0.31 | ±1.01 | ±0.10 | ±0.34 | ±2.86 |
| 120 | 0.87 | 0.65 | 2.33 | 0.49 | 8.85 | 66.92 |
| | ±0.28 | ±0.11 | ±1.20 | ±0.57 | ±1.18 | ±7.72 |

*Values are mean ± S.D. for 6 mice at each time period post injection.

I claim:
1. A compound of the formula

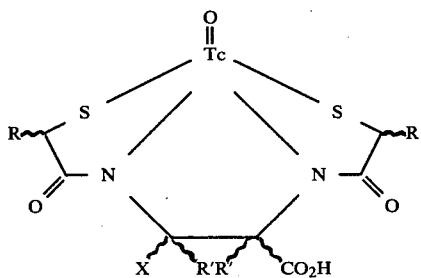

wherein X is carboxyl or hydrogen, R and R' are hydrogen or lower alkyl and the Tc is Tc-99m, and water-soluble salts thereof.

2. A compound according to claim 1 wherein R is hydrogen.

3. A compound according to claim 1 wherein X is carboxyl.

4. A compound according to claim 1 wherein X is hydrogen.

5. A compound according to claim 1 wherein R' is hydrogen.

6. A compound according to claim 1 wherein R and R' are hydrogen.

7. A compound according to claim 1 wherein R and R' are lower alkyl.

8. A compound according to claim 1 wherein R' is hydrogen and R is lower alkyl.

* * * * *